United States Patent [19]
Klotz

[11] Patent Number: 5,529,575
[45] Date of Patent: Jun. 25, 1996

[54] PREFABRICATED THERAPEUTIC PROSTHESIS FOR BELOW-KNEE AMPUTEES

[75] Inventor: John S. Klotz, Belleville, Ill.

[73] Assignee: Southern Illinois Prosthetic and Orthotic Ltd., Troy, Ill.

[21] Appl. No.: 419,045

[22] Filed: Apr. 10, 1995

[51] Int. Cl.$^6$ .................. A61F 2/78; A61F 2/80
[52] U.S. Cl. .......................... 623/33; 623/35
[58] Field of Search ................ 623/32, 33, 34, 623/35, 36; 602/23, 60, 62, 72, 63

[56] References Cited

U.S. PATENT DOCUMENTS

| | | | |
|---|---|---|---|
| 1,071,149 | 8/1913 | Erickson . | |
| 2,229,728 | 1/1941 | Eddels . | |
| 3,889,301 | 6/1975 | Bonner, Sr. . | |
| 4,128,903 | 12/1978 | Marsh et al. . | |
| 4,268,922 | 5/1981 | Marsh et al. . | |
| 4,842,608 | 6/1989 | Marx et al. | 623/33 |
| 4,872,879 | 10/1989 | Shamp | 623/36 |
| 4,988,360 | 1/1991 | Shamp | 623/33 |
| 5,108,455 | 4/1992 | Telikicherla | 623/33 |
| 5,211,667 | 5/1993 | Danforth | 623/35 |
| 5,246,464 | 9/1993 | Sabolich | 623/33 |
| 5,376,129 | 12/1994 | Faulkner et al. | 623/35 |

FOREIGN PATENT DOCUMENTS

| | | | |
|---|---|---|---|
| 0401710 | 12/1990 | European Pat. Off. | 623/32 |
| 2512666 | 3/1983 | France | 623/32 |
| 2103490 | 2/1983 | United Kingdom | 623/33 |

*Primary Examiner*—David H. Willse
*Assistant Examiner*—Bruce E. Snow
*Attorney, Agent, or Firm*—Grace J. Fishel

[57] ABSTRACT

A below-knee prosthesis for immediate post-operative use includes a shrinker socket and a frame fitting and following the contours of the lower socket into which the shrinker socket can be slid and secured. The prosthesis fits most below-knee amputees when provided in a minimal number of sizes. The shrinker socket has inner and outer nesting shells, the inner shell following the contours of an amputation stump and being open anteriorly and having a cut-out with outwardly bowed sidewalls forming a guard for the popliteal area and flanking medial and lateral hamstrings. The outer shell follows the contours of the patient's amputation stump anteriorly with a cut-out for the patient's patella and a channel over the patellar tendon. The outer shell otherwise follows the contours of the inner shell and has lateral and medial slits through which the shrinker socket can be compressed in the medial/lateral direction for applying a mild compression for suppressing edema in the stump and for applying pressure along medial and lateral positions of the stump as the patient puts weight thereon.

8 Claims, 4 Drawing Sheets

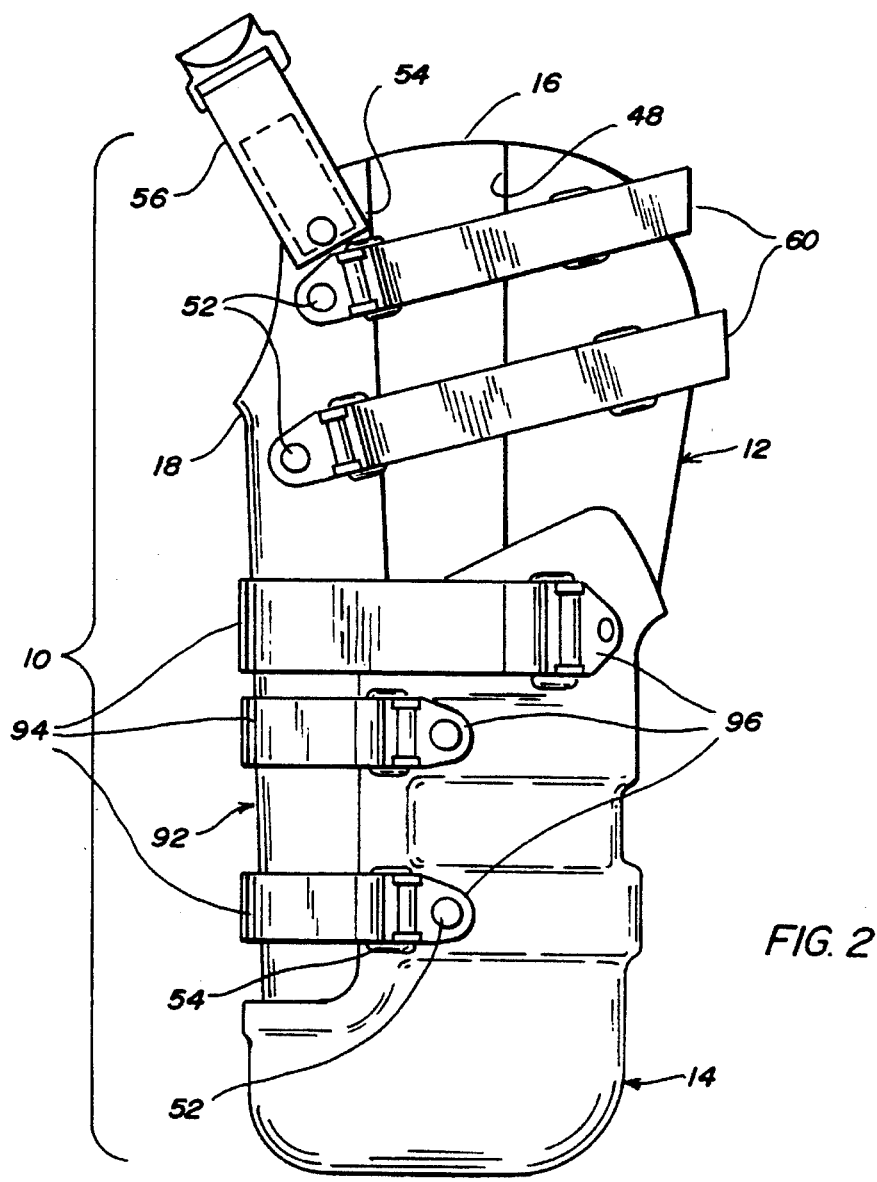
FIG. 2
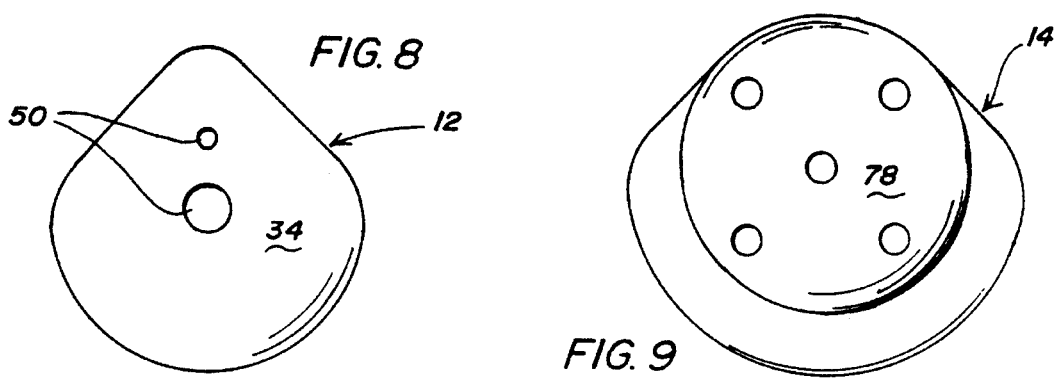
FIG. 8
FIG. 9

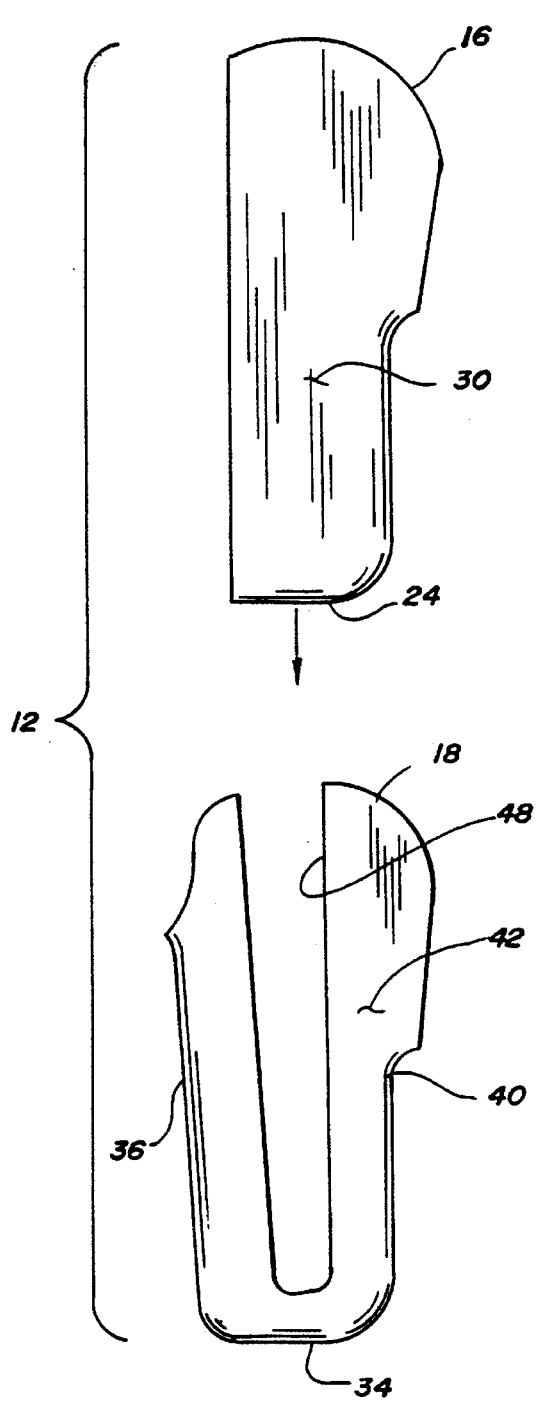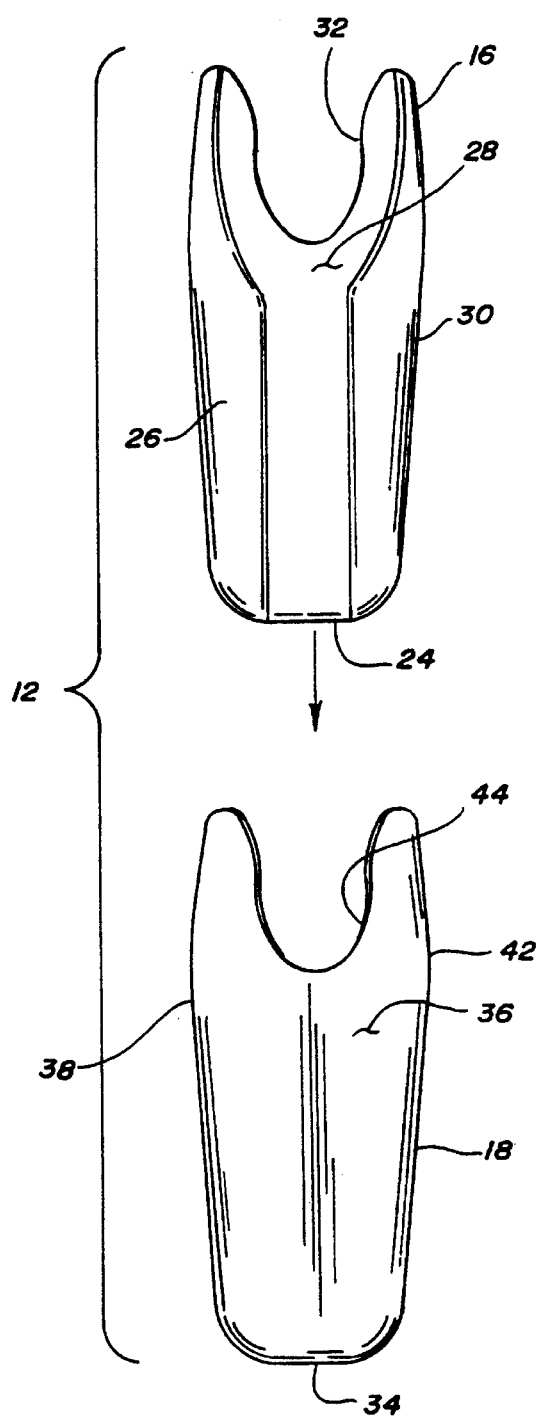
FIG. 3
FIG. 4

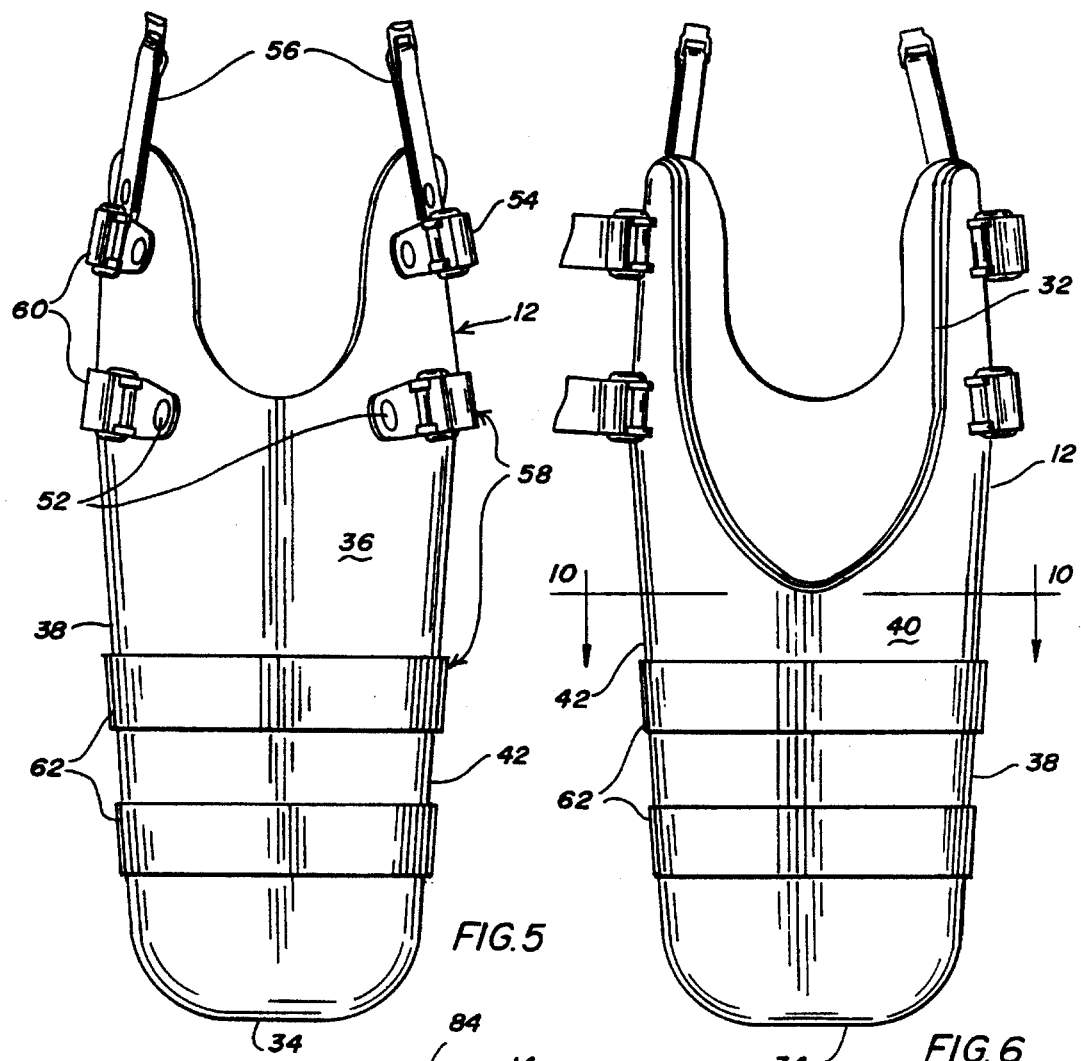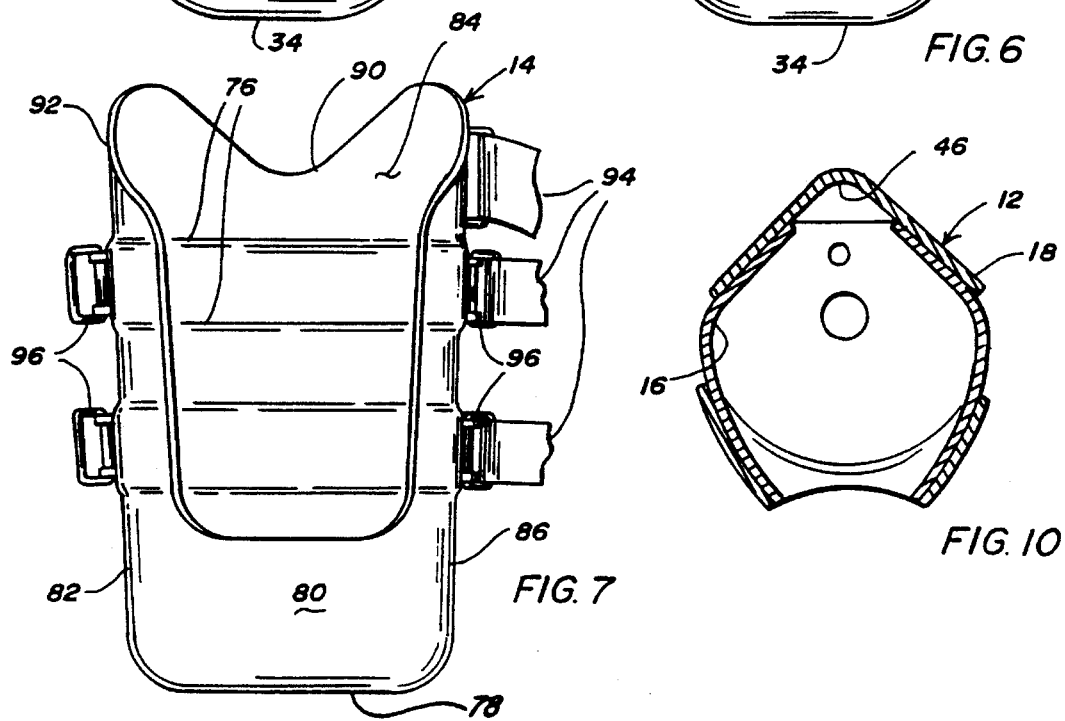

PREFABRICATED THERAPEUTIC PROSTHESIS FOR BELOW-KNEE AMPUTEES

BACKGROUND OF THE INVENTION

1. Field of the Invention

The present invention relates to a prefabricated therapeutic prosthesis for below-knee amputees and to a set of such prostheses adapted to fit most below-knee amputees.

2. Brief Description of the Prior Art

After a below-knee amputation, the residuum swells with edema and then, as healing progresses, gradually shrinks over a period of time. Because the diameter of the residuum changes, a series of therapeutic prostheses must be provided until a definite prosthesis can be fitted. In addition to serving as a guard, a primary function of a therapeutic prosthesis is to apply pressure on the residuum, limiting the amount of fluids accumulating in the amputation site and reducing the amount of post-operative edema. Another important function is to promote weight-bearing ambulation.

The loss of a lower extremity by amputation has profound physical and psychological consequences. Early ambulation is extremely important to the physical and psychological rehabilitation of the amputee. In the past, therapeutic prostheses have been relatively narrow in the anterior/posterior dimension such that the popliteal area is compressed and the patient's weight carried on the patella. Pressure on the popliteal area interferes with blood circulation necessary for healing and pulling on the medial and lateral hamstrings flanking the area tends to spread open the incision as the patient puts weight on his or her amputated leg.

Many post-amputative patients are old and are so weak that they cannot walk on one leg with crutches or a walker. The supplemental support of a lightweight, temporary prosthesis, on which the patient can bear weight, can make a critical difference between ambulation or bed-chair confinement, with its attendant complications. In the past, therapeutic prostheses have been made based on a cast or on measurements taken from the patient, requiring the services of a skilled prosthesis. Because each therapeutic prosthesis must be custom-fitted to the individual patient, prosthesis design and fabrication has been quite expensive, which cost is likely to be a growing problem with increasing numbers of older citizens and emphasis on medical cost containment.

SUMMARY OF THE INVENTION

In view of the above, it is an object of the present invention to provide a set of prefabricated therapeutic prostheses that will fit most below-knee amputees. It is another object to provide a shrinker socket for placement about a patient's amputation stump that does not apply pressure on the patient's patellar tendon or on his or her popliteal area and flanking medial and lateral hamstrings. It is also an object to provide a shrinker socket with little tendency to open the stump incision as the patient puts weight on the stump. Other objects and features of the invention will be in part apparent and in part pointed out hereinafter.

In accordance with the invention, a below-knee prosthesis for immediate post-operative use includes a shrinker socket for placement about a patient's amputation stump. The shrinker socket is open topped and is formed from nesting inner and outer shells. The inner shell is generally pentagonal in cross-section and configured to conform to the patient's stump and is open anteriorly. Starting in the popliteal area, the inner shell has a posterior V-shaped notch opening upwardly with outwardly bowed side edges configured to form a protective guard over the patient's popliteal area and medial and lateral hamstrings flanking the popliteal area. The outer shell is generally configured to conform to the patient's stump anteriorly and is otherwise conformed to the inner shell. The outer shell has an anterior U-shaped notch configured to expose the patient's patella and a channel forming a protective guard over the patient's patellar tendon. The outer shell also has lateral and medial slits with fastening adjustment means for selectively opening and closing the slits. When the fastening adjustment means are loosened, the shrinker socket can be spread open and relatively painlessly slipped on and off the patient's stump. When the slits are closed with the fastening adjustment means, the shrinker socket applies a mild compression for suppressing edema in the stump and puts pressure on the medial and lateral portions of the stump as the patient puts weight on the stump. The inner and outer shells are joined posteriorly of the slits.

The invention summarized above comprises the constructions hereinafter described, the scope of the invention being indicated by the subjoined claims.

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 2 is an assembled side elevation of the below-knee prosthesis;

FIG. 3 is an exploded lateral elevation of the shrinker socket;

FIG. 4 is an exploded anterior elevation of the shrinker socket;

FIG. 5 is a front elevation of the shrinker socket;

FIG. 6 is a rear elevation of the shrinker socket;

FIG. 7 is a front elevation of the frame;

FIG. 8 is a bottom view of the shrinker socket;

FIG. 9 is a bottom view of the frame; and,

FIG. 10 is a section taken along line 10—10 in FIG. 6.

DETAILED DESCRIPTION OF THE INVENTION

Figure 1:
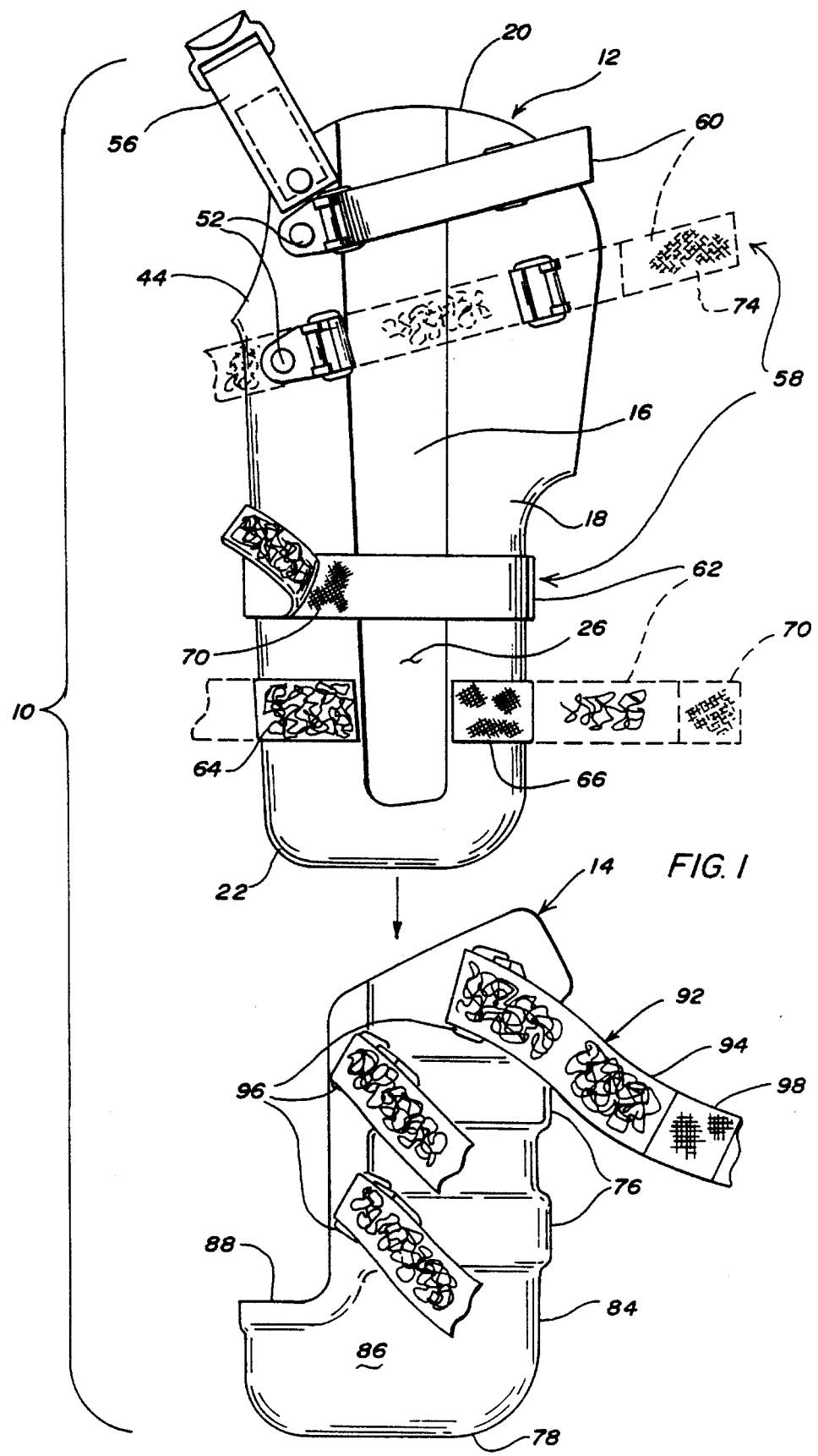
FIG. 1 is an exploded side elevation of a below-knee prosthesis including a shrinker socket (with inner and outer shells assembled) and a frame in accordance with the present invention.

Referring to the drawings, more particularly by reference number, reference numeral 10 refers to a below-knee prosthesis in accordance with the present invention. Prosthesis 10 includes a removable shrinker socket 12 for placement about a patient's amputation stump or residuum and a weight bearing frame 14 into which the shrinker socket is received.

Shrinker socket 12 is compressible and relatively narrow in the medial/lateral dimension as compared to the anterior/posterior. Shrinker socket 12 is formed of nesting inner and outer shells 16, 18 and is open ended at its proximate end 20 to facilitate insertion of the residuum and rounded, closed at its distal end 22 to equalize the pressure on the bottom end of the stump. Inner shell 16 is generally pentagonal in cross-section (See FIG. 10) and has a bottom wall 24, generally arcuate in cross-section, and is open anteriorly with upwardly extending medial, posterior and lateral walls 26, 28, 30, respectively. Medial and lateral walls 26 and 30 are configured to conform to the anatomical contours of the patient's residuum and project upwardly beyond and above the knee joint to provide condylar support. Posterior wall 28 is also configured to conform to the patient's residuum and curvilinearly merges into medial and lateral walls below the popliteal area. Then, starting in the popliteal area, posterior wall 28 curves outwardly into a wide V-shaped notch 32 opening at the proximate end of shrinker socket 12, posterior wall 28 gradually becoming integral with medial and lateral walls 26 and 30. Outwardly bowed posterior wall 28 around V-shaped notch 32 is biomechanically engineered to provide a protective guard around the popliteal area and flanking medial and lateral hamstrings. As little of posterior wall 28 is cut away by notch 32 as possible so as to exert maximal counter pressure on the back of the residuum.

Outer shell 18 has a bottom wall 34, generally arcuate in cross-section, conforming with bottom wall 24 of inner shell 16 and with upwardly extending anterior, medial, posterior and lateral walls 36, 38, 40, and 42, respectively. Anterior wall 36 has a U-shaped notch 44 configured to expose the patella and to conform to the anatomical contours of the patient's residuum except that starting in the bight of V-shaped notch the anterior wall bows outwardly forming a shallow V-bottomed channel 46 configured to run from the patellar tendon to the distal end of the tibia. Channel 46 is biomechanically engineered to provide a protective guard around the tendon. Medial, posterior and lateral walls 38, 40 and 42 of outer shell 18 match the contours of medial, posterior and lateral walls 26, 28, 30 of inner shell 16 including the shape of V-shaped notch 32. Medial and lateral walls of inner shell 26 and 30 have tapering edges toward outer shell 18 so that when overlapped with the outer shell 18, the overlapping does not cause bulging which would cause pain due to areas of localized pressure. A slit 48 is provided in each of medial and lateral walls 38, 42 of outer shell 18, exposing counterpart medial and lateral walls 26, 30 of inner shell 16. Slits 48 start at the proximate end of the shrinker socket and run substantially or entirely to the distal end of the outer shell permitting shrinker socket to be opened up to facilitate sliding entry of a stump while vent holes 50 are provided in bottom walls 24, 34 to permit the escape of air as the residuum is slid into shrinker socket 12. Rivets 52 join inner and outer shells 16, 18 together posterior of slits 48 and secure turnbuckles 54. An opposing set of turnbuckles 54 are attached to outer shell 18 anterior of slits 48. A pair of hooks 56 may also be attached with rivets 52 for attachment to an elastic waist band (not shown) worn by the patient for supporting the shrinker socket.

Fastening adjustment means 58 are provided for selectively opening and closing slits 48 so that shrinker socket 12 can be spread open and relatively painlessly slipped on and off the patient's stump and so that the shrinker socket can be secured closed around the stump applying a mild compression for suppressing edema and for applying pressure along the medial and lateral portions of the stump as the patient puts weight on the stump. The fastening adjustment means 58 comprise six belts, divided into an upper set 60 of four belts and a lower set 62 of two belts, each of material having pile on one side and interlocking hooks on the other side, for example VELCRO. Each belt in lower set 62 is attached to a strip 64 of material of a first gender that encircles and is affixed to outer shell 18 anteriorly of slits 48 and a second strip 66 of material of opposite gender that encircles and is affixed to outer shell 18 posteriorly of slits 48. Each belt in lower set has first and second ends and is formed of one gender of material with a patch 70 of material of opposite gender on the front and back sides of the first end. Patch 70 adheres to one of strips 64, 66 of opposite gender and belt 62 is wrapped around shrinker socket 12, adhering to one of first or second strips 64, 66 of opposite gender and then to patch 70, closing or pinching slits 48 closed by the desired amount. Each belt in upper set 60 has first and second ends and is formed of one gender of material with a patch 74 of material of opposite gender on the front and back sides of the first end. Each strap 72 is wound through a selected pair of turnbuckles 54 on opposite sides of slit, cinched tight by the desired amount and adhered to patch 74.

Frame 14 has an internal contour matching the external contour of the lower portion of shrinker socket 12, including the contour of lower belts 62 manifested as grooves 76. Frame 14 has a flat bottom wall 78 into which is seated a plate (not shown) by means of which a pylon or artificial leg shaft outfitted with a foot/ankle assembly or walking tip can be attached. Frame has anterior, medial, posterior and lateral walls 80, 82, 84 and 86, respectively. A deep U-shaped notch 88 is formed in anterior wall 80 exposing shrinker socket 12 and a shallow V-shaped notch is formed in posterior wall 90, tracking that in inner and outer shells 16, 18.

Fastening attachment means 92 are provided for selectively securing shrinker socket 12 in frame 14. The fastening attachment means 92 are illustrated as three belts, each of material having pile on one side and interlocking hooks on the other side, for example VELCRO. When fastening attachment means 92 are loosened, shrinker socket 20 can slide freely in and out of frame 14. Three turnbuckles 96 are provided along the side edges of U-shaped notch 88, adjusted with rivets 52. Each of belts 94 has first and second ends and is formed of one gender of material with a patch 98 of material of opposite gender on the front and back sides of the first end. Each belt 94 is wound through a selected pair of turnbuckles 96, drawn tight securing shrinker socket 12 in frame 14 and adhered to patch 98.

Prosthesis 10 is presently formed by a technique known as drape-forming. It will be understood, however, that it could be made by injection molding or any other suitable plastic forming process. As a first step, a positive cast is made of the patient's residuum. Older ways of doing this include making a plaster negative from which is formed the positive. Modern methods involve use of a computer aided design/computer aided manufacture (CAD/CAM) system which models a three-dimensional image of the residuum in the computer's memory based measurements or a camera/laser image providing details thereof. The data can be adjusted using computer software to create a biomechanically correct shrinker socket contour, including the addition of V-bottomed channel 46 over the patellar tendon and outwardly bowed posterior walls 28 around V-shaped notch providing relief over the popliteal area and medial and lateral hamstrings. The positive cast is created from a foam blank using the modified data and a computer controlled lathe or alternatively, the data is not modified and biomechanical adjustment made after the positive cast is cut by building up the areas to be protected.

In forming shrinker socket 12, a sheet of semi-rigid plastic, such as low density polyethylene, is heated in a oven and when softened, draped over the positive cast, while a partial vacuum is being applied to the cast to draw the plastic into contact with the exterior surface of the cast, forming inner shell 16. A mold release material is applied to the outer surface of inner shell 16 and a second sheet of heated plastic is draped over the first, as before, forming outer shell 18.

Inner and outer shells 16, 18 are separated, trimmed and the edges smoothed and/or tapered and rivets 52 holding turnbuckles 54 attached to outer shell anterior of slits 48. After hooks 56 are attached, inner and outer shells 16, 18 are assembled and joined with rivets 52 along with turnbuckles 54. Strips 64, 66 are glued to the outer shell 18 and belts 60 woven through turnbuckles 54. Frame 14 is formed from a sheet of rigid plastic, such as polypropylene, which is heated and when softened, draped over the finished shrinker socket 12. Frame 14 is trimmed and the edges smoothed, turnbuckles 96 applied and belts woven through the turnbuckles 96, finishing prosthesis 10.

Instead of custom-forming each prosthesis, it is preferred that they be mass produced in a series of at least three sizes, small, medium and large, each of right and left limb design to accommodate most adult below-knee amputees and substantially all with the addition of extra-small and extra-large sizes. The length and diameter of the shrinker sockets in the set are given in the following tables, measurements starting at mid patellar tendon (MPT).

TABLE I

| Size | Length (mm) |
| --- | --- |
| x small | 150 |
| small | 158 |
| medium | 165 |
| large | 173 |
| x large | 180 |

TABLE II

| mm below MPT | Size (mm) | | | | |
| --- | --- | --- | --- | --- | --- |
| | x small | small | medium | large | x large |
| 0 | 280 | 315 | 345 | 380 | 410 |
| 30 | 270 | 305 | 335 | 370 | 400 |
| 60 | 280 | 315 | 345 | 380 | 410 |
| 90 | 290 | 320 | 355 | 390 | 420 |
| 120 | 300 | 325 | 360 | 395 | 425 |
| 150 | — | — | — | — | 430 |

In use, the residuum of a recent amputee is measured and a prefabricated shrinker socket 12 larger but closest in size to the stump selected from the set of shrinker sockets whose dimensions are given in the above tables, together with a mating frame 14. The stump is dressed with a clean sock, additional socks being added to achieve a snug fit and a pad of lambs' wool or other resilient material is put into the bottom of the shrinker socket. With fastening adjustment means 58 loosened, slits 48 can be spread open and the residuum slid into the shrinker socket relatively painlessly. The U-shaped notch 44 for the patella should be aligned and shrinker socket pushed up until the amputee feels light pressure against the end of the residuum. The fastening adjustment means are then tightened so that shrinker socket 12 applies a mild compression for suppressing edema in the stump. At this point, the patient should be able to bend his or her knee with no obstruction or with no pressure on the patellar tendon, popliteal area and flanking medial and lateral hamstrings. With frame 14 attached to a pylon and foot for walking or the like, fastening attachment means 92 are loosened so that shrinker socket 12 can slide easily into the frame. Fastening attachment means are then tightened securing the shrinker socket in the frame, restraining shrinker socket from sliding movement by belts 62 which are held in grooves 76. As the patient puts weight on the stump, shrinker socket 12 applies pressure along the medial and lateral portions of the stump, avoiding pressure on the anterior and posterior portions which would tend to tear open the medial to lateral incision. As healing progresses, the patient should be remeasured when five socks are necessary to maintain a snug fit and a determination made whether a second (or possibly even a third), smaller shrinker socket is necessary before fitting a definitive prosthesis.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A below-knee prosthesis for immediate post-operative use comprises a shrinker socket for placement about a patient's amputation stump, said shrinker socket comprising open topped, nesting inner and outer shells, said inner shell generally pentagonal in cross-section and configured to conform to the patient's residuum and being open anteriorly, said inner shell being narrower in cross-section in a medial/lateral dimension than in an anterior/posterior direction and, said inner shell having a posterior V-shaped notch with side edges configured to start in the popliteal area and opening upwardly and outwardly configured to form a protective guard over the patient's popliteal area and medial and lateral hamstrings flanking the popliteal area, said outer shell generally configured to conform to the patient's residuum anteriorly and otherwise conformed to the inner shell, said outer shell having an anterior U-shaped notch configured to conform to the patient's patella and a channel configured to form a protective guard over the patient's patellar tendon, said outer shell having a lateral and medial slit and fastening adjustment means for selectively opening and closing the slits so that the shrinker socket can be spread open and relatively painlessly slipped on and off the patient's stump and secured around the stump to apply a mild compression for suppressing edema in the stump and for applying pressure along medial and lateral portions of the stump as the patient puts weight on the stump, said inner and outer shells joined posteriorly of the slits.

2. The prosthesis of claim 1 further including a frame into which the shrinker socket is received, said frame comprising an open topped shell with an internal contour matching the external contour of a lower portion of the shrinker socket into which the shrinker socket can slide and fastening attachment means for securing the shrinker socket in the frame.

3. The prosthesis of claim 2 wherein the fastening attachment means comprise at least one belt formed of hook and pile material wrapped around the lower portion of the shrinker socket and at least one pair of belts formed of hook and pile material, one member of each pair woven through a pair of turnbuckles on opposite sides of the medial and lateral slits on the upper portion of the shrinker socket.

4. A below-knee prosthesis for immediate post-operative use comprises a shrinker socket with a proximate and a distal end for placement about a patient's amputation stump, said shrinker socket comprising open topped, nesting inner and outer shells, said inner shell generally pentagonal in cross-section and open anteriorly, said inner shell being narrower in cross-section in a medial/lateral dimension than in an anterior/posterior direction and having a bottom wall generally arcuate in cross-section and upwardly extending medial, posterior and lateral walls, said medial and lateral walls configured to conform to the patient's stump and projecting upward beyond and above the patient's knee joint to provide condylar support, said posterior wall configured to conform to the patient's stump below the patient's popliteal area and then curving outwardly into a wide V-shaped notch forming a protective guard over the patient's popliteal area and medial and lateral hamstrings flanking the popliteal area and gradually becoming integral with the medial and lateral walls, said outer shell having a bottom wall generally arcuate in cross-section and conforming with the bottom wall of the inner shell and upwardly extending anterior, medial, posterior and lateral walls, said anterior wall configured to conform to the patient's stump and having a V-shaped notch configured to expose the patient's patella and a shallow channel configured to form a protective guard over the patient's patellar tendon and said medial, posterior and lateral walls conforming with the medial, posterior and lateral sidewalls walls of the inner shell, said outer shell having a slit in the medial and lateral sidewalls starting at the proximate end of the shrinker socket and running substantially to the distal end, and fastening adjustment means for selectively opening and closing the slits so that the shrinker socket can be spread open and relatively painlessly slipped on and off the patient's stump and secured around the stump to apply a mild compression for suppressing edema in the stump and for applying pressure along medial and lateral portions of the stump as the patient puts weight on the stump, said inner and outer shells joined posteriorly of the slits.

5. The prosthesis of claim 4 wherein the fastening attachment means comprise at least one belt formed of hook and pile material wrapped around the lower portion of the shrinker socket and at least one pair of belts formed of hook and pile material, one member of each pair woven through a pair of turnbuckles on opposite sides of the medial and lateral slits on the upper portion of the shrinker socket.

6. The prosthesis of claim 5 further including a frame into which the shrinker socket is received, said frame comprising an open topped shell with an internal contour matching the external contour of a lower portion of the shrinker socket into which the shrinker socket can slide and fastening attachment means for securing the shrinker socket in the frame.

7. A set of shrinker sockets for immediate post-operative use adapted to fit a residuum of many below-the-knee amputees including a small, medium and large size of both left and right design, each shrinker socket comprising open topped, nesting inner and outer shells, said inner shell generally pentagonal in cross-section and configured to conform to the patient's residuum and being open anteriorly, said inner shell being narrower in cross-section in a medial/lateral dimension than in an anterior/posterior direction and said inner shell having a posterior V-shaped notch with side edges configured to start in the popliteal area and opening upwardly and outwardly configured to form a protective guard over the patient's popliteal area and medial and lateral hamstrings flanking the popliteal area, said outer shell generally configured to conform to the patient's residuum anteriorly and otherwise conformed to the inner shell, said outer shell having an anterior U-shaped notch configured to expose the patient's patella and a channel configured to form a protective guard over the patient's patellar tendon, said outer shell having a lateral and medial slit and fastening adjustment means for selectively opening and closing the slits so that the shrinker socket can be spread open and relatively painlessly slipped on and off the patient's residuum and secured around the residuum to apply a mild compression for suppressing edema in the residuum and for applying pressure along medial and lateral portions of the residuum as the patient puts weight on the residuum, said inner and outer shells joined posteriorly of the slits, said small size shrinker socket configured to fit a residuum having a circumference at the mid patellar tendon of up to about 315 mm, 30 mm below mid patellar tendon up to about 305 mm, 60 mm below mid patellar tendon up to about 315 mm, 90 mm below mid patellar tendon up to about 320 mm and 120 mm below mid patellar tendon up to about 325 mm, said medium size shrinker socket configured to fit a residuum having a circumference at the mid patellar tendon of up to about 345 mm, 30 mm below mid patellar tendon up to about 335 mm, 60 mm below mid patellar tendon up to about 345 mm, 90 mm below mid patellar tendon up to about 355 mm and 120 mm below mid patellar tendon up to about 360 mm, and said large size shrinker socket configured to fit a residuum having a circumference at the mid patellar tendon of up to about 380 mm, 30 mm below mid patellar tendon up to about 370 mm, 60 mm below mid patellar tendon up to about 380 mm, 90 mm below mid patellar tendon up to about 390 mm and 120 mm below mid patellar tendon up to about 395 mm.

8. The shrinker sockets of claim 7 wherein the small size shrinker socket is configured to fit a residuum up to about 158 in length, the medium size shrinker socket is configured to fit a residuum up to about 165 mm in length and the large size shrinker socket is configured to fit a residuum up to about 173 mm in length.

* * * * *